US012708602B2

(12) United States Patent
Lee

(10) Patent No.: US 12,708,602 B2
(45) Date of Patent: Aug. 18, 2026

(54) FERMENTATION EXTRACTS, COSMETIC COMPOSITION AND MANUFACTURING METHOD OF FERMENTATION EXTRACTS

(71) Applicant: bioMOA Medical, Inc., Suwon-si (KR)

(72) Inventor: Dong-Han Lee, Gunpo-si (KR)

(73) Assignee: bioMOA Medical, Inc., Suwon-si (KR)

( * ) Notice: Subject to any disclaimer, the term of this patent is extended or adjusted under 35 U.S.C. 154(b) by 301 days.

(21) Appl. No.: 18/646,804

(22) Filed: Apr. 26, 2024

(65) Prior Publication Data

US 2025/0144005 A1 May 8, 2025

(30) Foreign Application Priority Data

Nov. 2, 2023 (KR) ........................ 10-2023-0149724

(51) Int. Cl.

| | |
|---|---|
| ***A61K 8/99*** | (2017.01) |
| ***A61K 8/14*** | (2006.01) |
| ***A61K 8/64*** | (2006.01) |
| ***A61K 8/65*** | (2006.01) |
| ***A61Q 19/00*** | (2006.01) |
| ***C12N 1/20*** | (2026.01) |

(52) U.S. Cl.

CPC .................. *A61K 8/99* (2013.01); *A61K 8/14* (2013.01); *A61K 8/64* (2013.01); *A61K 8/65* (2013.01); *A61Q 19/00* (2013.01); *C12N 1/20* (2013.01); *A61K 2800/10* (2013.01); *A61K 2800/85* (2013.01)

(58) Field of Classification Search

CPC . A61K 8/99; A61K 8/14; A61K 8/365; A61K 2800/10; C12N 1/20

USPC .......................................................... 424/401

IPC ................................................... A61K 2800/10

See application file for complete search history.

(56) References Cited

FOREIGN PATENT DOCUMENTS

| | | | | |
|---|---|---|---|---|
| KR | 101394230 B1 | 5/2014 | | |
| KR | 101895174 B1 | 9/2018 | | |
| KR | 102139471 B1 | 7/2020 | | |
| KR | 102324480 B1 | 11/2021 | | |
| KR | 102386262 | * | 4/2022 | ........... A61K 8/9789 |
| KR | 102538693 B1 | 6/2023 | | |

* cited by examiner

*Primary Examiner* — Walter E Webb

(74) *Attorney, Agent, or Firm* — NKL Law; Jae Youn Kim

(57) ABSTRACT

Provided are fermentation extracts, cosmetic composition, and manufacturing method of fermentation extracts. For this, the present invention discloses a fermentation extract consisting of a glutathione liquid dispersion liposomized using a liquid collagen extract as a solvent and a *Lactobacillus* fermentation filtrate obtained by stirring and extracting the same at a preset low temperature.

11 Claims, 8 Drawing Sheets

| Extraction conditions of low-molecular weight extract | | | | | | | | |
|---|---|---|---|---|---|---|---|---|
| No | Temperatu re | Extraction time | Specific observations during extraction | Results | | | | |
| | | | | Day 1 | Day 3 | Day 7 | Day 20 | Day 40 |
| 1 | 60℃ | 100 | Aggregation of raw material collagen occurred during extraction | | | | - | - |
| 2 | 50℃ | | - | - | - | - | Precipitation occurred | - |
| 3 | 40℃ | | - | - | - | - | Precipitation occurred | - |
| 4 | 30℃ | | - | - | - | - | Precipitation occurred | - |
| 5 | 20℃ | | - | - | - | - | - | Precipitation occurred |
| 6 | 10℃ | | Long time required for dissolving raw material collagen during extraction | - | - | Precipitation occurred | - | - |

FIG. 1

| Extraction conditions of collagen extraction | | | | | | | | | | |
|---|---|---|---|---|---|---|---|---|---|---|
| No | Temperature | Extraction time | Specific observations during extraction | Results | | | | | | |
| | | | | Day 1 | Day 3 | Day 7 | Day 20 | Day 40 | Day 60 | Day 100 |
| 1 | 20℃ | 50 | - | - | - | - | Precipitation occurred | - | - | - |
| 2 | | 100 | - | - | - | - | - | Precipitation occurred | - | - |
| 3 | | 150 | - | - | - | - | - | Precipitation occurred | - | - |
| 4 | | 200 | - | - | - | - | - | - | Precipitation occurred | - |
| 5 | | 250 | - | - | - | - | - | - | - | - |
| 6 | | 300 | - | - | - | - | - | - | - | - |

FIG. 2

| High-content glutathione mixed | | | |
|---|---|---|---|
| No | Item | Content | Day 1 |
| 1 | Glutathione powder used | 1% | Precipitation occurred |
| 2 | Glutathione powder used | 3% | Precipitation occurred |
| 3 | Glutathione powder used | 5% | Precipitation occurred |
| 4 | Glutathione powder used | 10% | Precipitation occurred |

FIG. 3

| High-content liposome glutathione mixed | | | | | | | | |
|---|---|---|---|---|---|---|---|---|
| No | Item | Content | Day 1 | Day 3 | Day 7 | Day 20 | Day 40 | Day 60 |
| 1 | Liposome glutathione used | 1% | - | Precipitation occurred | - | - | - | - |
| 2 | Liposome glutathione used | 3% | - | - | Precipitation occurred | - | - | - |
| 3 | Liposome glutathione used | 5% | - | - | Precipitation occurred | - | - | - |
| 4 | Liposome glutathione used | 10% | - | - | - | - | - | - |

FIG. 4

| Lactobacillus fermentation filtrate | | | | | | | | | |
|---|---|---|---|---|---|---|---|---|---|
| No | Item | Fermentation time | Results | | | | | | |
| | | | Day 1 | Day 3 | Day 7 | Day 20 | Day 40 | Day 60 |
| 1 | Lactobacillus fermentation solution | 10 | - | - | - | - | - | - |
| 2 | Lactobacillus fermentation solution | 15 | - | - | - | Off-flavor generated | - | - |
| 3 | Lactobacillus fermentation solution | 20 | - | - | Off-flavor generated | - | - | - |

FIG. 5

| Low-temperature stirring and extraction | | | | | | |
|---|---|---|---|---|---|---|
| No | Temperature | Extraction time | Results | | | |
| | | | Day 1 | Day 3 | Day 7 | Day 20 |
| 1 | 60℃ | 100 | Off-flavor generated from Lactobacillus fermentation solution | - | - | - |
| 2 | 50℃ | | Off-flavor generated from Lactobacillus fermentation solution | - | - | - |
| 3 | 40℃ | | - | Off-flavor generated from Lactobacillus fermentation solution | - | - |
| 4 | 30℃ | | - | - | - | Off-flavor generated from Lactobacillus fermentation solution |
| 5 | 20℃ | | - | - | - | Glutathione precipitated |
| 6 | 10℃ | | Glutathione precipitated | - | - | - |

FIG. 6

| Low-temperature stirring and extraction | | | | | | | | | |
|---|---|---|---|---|---|---|---|---|---|
| No | Temperature | Extraction time | Results | | | | | | |
| | | | Day 1 | Day 3 | Day 7 | Day 20 | Day 40 | Day 60 | Day 100 |
| 1 | 25℃ | 50 | Glutathione precipitated | - | - | - | - | - | - |
| 2 | | 100 | - | - | Glutathione precipitated | - | - | - | - |
| 3 | | 150 | - | - | - | - | Glutathione precipitated | - | - |
| 4 | | 200 | - | - | - | - | Glutathione precipitated | - | - |
| 5 | | 250 | - | - | - | - | - | Glutathione precipitated | - |
| 6 | | 300 | - | - | - | - | - | - | - |

FIG. 7

FERMENTATION EXTRACTS, COSMETIC COMPOSITION AND MANUFACTURING METHOD OF FERMENTATION EXTRACTS

BACKGROUND OF THE INVENTION

Field of the Invention

The present invention relates to fermentation extracts, cosmetic composition, and manufacturing method of fermentation extracts.

Description of the Related Art

When an collagen extract is used alone as a single ingredient in a cosmetic composition, it has some wrinkle improvement and elasticity-enhancing effects, but the collagen extract itself has a poor moisturizing effect and is difficult to improve a skin-whitening effect.

PRIOR ART DOCUMENT (Patent Document 0001) KR 10-2139471
(Patent Document 0002) KR 10-2538693

SUMMARY OF THE INVENTION

Therefore, the present invention was created to solve the problems described above, and an object of the present invention is to provide the best naturally obtainable moisturizing factor because a natural moisturizing factor, which is lactic acid formed during the fermentation process using *Lactobacillus* fermentation filtrate, is produced. In addition, modern cosmetics are basically dual-functional cosmetics such as having the functions of whitening and wrinkle improvement, so the skin-whitening effect is also an important function. Therefore, the object of the present invention is to enhance a whitening effect by preparing a liposomized glutathione liquid, and to enhance a whitening effect and a moisturizing effect by extracting once again the *Lactobacillus* fermentation filtrate and the liposomized glutathione liquid using a liquid collagen extract extracted at a low temperature.

However, the objects of the present invention are not limited to the objects mentioned above, and other objects not mentioned will be clearly understood by those skilled in the art from the description below.

The above-described object of the present invention may be achieved by providing a fermentation extract consisting of a glutathione liquid dispersion liposomized using a liquid collagen extract as a solvent and a *Lactobacillus* fermentation filtrate obtained by stirring and extracting the same at a preset low temperature.

In addition, the preset low temperature is 25° C.

In addition, the liquid collagen extract is extracted at a low temperature of 20° C. by mixing collagen powder, butylene glycol, and purified water at a preset ratio.

In addition, the liposomized glutathione liquid dispersion is a dispersion obtained by mixing and stirring purified water and glutathione powder at a preset ratio.

In addition, the *Lactobacillus* fermentation filtrate is a filtrate obtained by mixing purified water, a *Lactobacillus* fermentation solution, and glycerin at a preset ratio and fermenting.

Meanwhile, the purpose of the present invention may be achieved by providing a cosmetic composition including a fermentation extract as an active ingredient.

Meanwhile, the object of the present invention may be achieved by providing a manufacturing method of a fermentation extract using dual low-temperature extraction and liposomization, the method including: a step of producing a liquid collagen extract at a first low temperature by mixing collagen powder, butylene glycol, and purified water at a preset ratio; a step of producing a liposomized glutathione liquid dispersion by mixing and stirring purified water and glutathione powder at a preset ratio; a step of producing a *Lactobacillus* fermentation filtrate obtained by mixing purified water, a *Lactobacillus* fermentation solution, and glycerin at a preset ratio and fermenting; and a step of producing a fermentation extract by stirring and extracting a glutathione liquid dispersion liposomized using a liquid collagen extract as a solvent and a *Lactobacillus* fermentation filtrate at a second low temperature which is different from the first low temperature In addition, the step of producing a liquid collagen extract includes: a step of preparing low-molecular-weight collagen powder in a mesh screen of 400 mesh; a step of setting the temperature of an extractor to 20° C.; a step of placing a mesh screen containing 30 parts by weight of butylene glycol, 65 parts by weight of purified water, and 5 parts by weight of collagen powder into the extractor; a step of extracting in the extractor for 250 to 300 hours; and a step of filtering a completely extracted mixture through the mesh screen of 400 mesh to complete a liquid collagen extract extracted at a low temperature.

In addition, the step of producing a liposomized glutathione liquid dispersion includes: a step of preparing 90 parts by weight of purified water and 10 parts by weight of glutathione powder; a step of primarily mixing the purified water with the glutathione in a stirrer for 30 minutes; a step of producing a homogeneous dispersion by passing the primarily stirred mixed liquid through a ultra-high pressure emulsification process; and a step of filtering the homogeneous dispersion with a filter screen of 250 mesh to complete a liposomized glutathione liquid dispersion.

In addition, the step of producing a producing a *Lactobacillus* fermentation filtrate includes: a step of producing a *Lactobacillus* fermentation solution by preparing a *Lactobacillus* strain, inoculating the same into a liquid medium, maintaining the temperature of the liquid medium at 35 to 40° C., and culturing in an incubator for three days; a step of adding 50 parts by weight of purified water, 30 parts by weight of the *Lactobacillus* fermentation solution, and 20 parts by weight of glycerin into a fermenter and fermenting at 37° C. for ten hours; and a step of filtering the completely fermented product through a mesh screen of 400 mesh to complete a *Lactobacillus* fermentation filtrate.

In addition, the step of producing a fermentation extract includes: a step of setting the temperature of an extractor to 25° C.; a step of adding 60 parts by weight of a liquid collagen extract as a solvent, 20 parts by weight of liposomized glutathione liquid dispersion, and 20 parts by weight of the *Lactobacillus* fermentation filtrate into the extractor and mixing; a step of extracting for 300 hours while performing a stirring process; and a step of filtering the completely extract through a mesh screen of 400 mesh to complete a fermentation extract.

BRIEF DESCRIPTION OF THE DRAWINGS

The following drawings attached to the present specification illustrate a preferred embodiment of the present invention, and serve to further understand the technical idea of the present invention along with the detailed description of the invention. Therefore, the present invention should not be construed as being limited to the matters described in the drawings.

FIG. 1 shows an experimental example illustrating the results of an extraction experiment by temperature of low-molecular weight collagen according to one embodiment of the present invention;

FIG. 2 shows an experimental example illustrating the results of an extraction experiment according to extraction time at 25° C. according to one embodiment of the present invention;

FIG. 3 shows an experimental example illustrating the results of an experiment in which glutathione powder was dissolved in purified water according to one embodiment of the present invention;

FIG. 4 shows an experimental example illustrating the results of an experiment when dissolving liposome glutathione in purified water according to the liposome glutathione content according to one embodiment of the present invention;

FIG. 5 shows an experimental example for obtaining experimental results of a *Lactobacillus* fermentation solution according to fermentation time according to one embodiment of the present invention;

FIG. 6 shows an experimental example for obtaining experimental results during low-temperature stirring extraction according to temperature according to one embodiment of the present invention;

FIG. 7 shows an experimental example for obtaining experimental results during low-temperature stirring extraction according to extraction time according to one embodiment of the present invention.

DETAILED DESCRIPTION OF THE EMBODIMENTS

Figure 8:
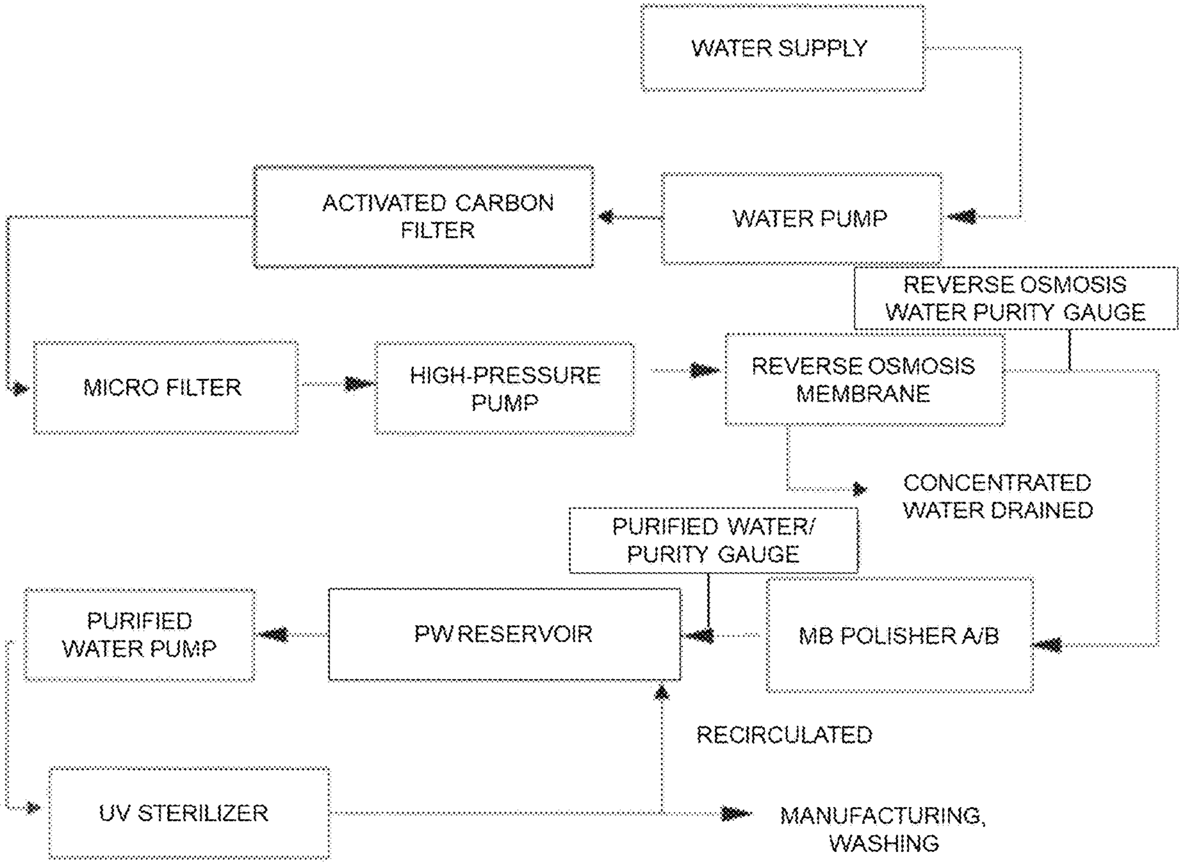
FIG. 8 shows a diagram illustrating a process for obtaining purified water according to one embodiment of the present invention.

Hereinafter, a preferred embodiment of the present invention will be described with reference to the drawings. In addition, the embodiment described below does not unduly limit the content of the present invention described in the claims, and all of the features described in the present embodiment may not be considered as essential as a solution of the present invention. In addition, the description of conventional technologies and matters that are obvious to those skilled in the art may be omitted, and the description of these omitted components (methods) and functions may be sufficiently referred without departing from the technical idea of the present invention.

A manufacturing method of fermentation extracts using double low-temperature extraction and liposomization according one an embodiment of the present invention is a manufacturing method of a fermentation extract that is good for moisturizing and whitening by using a glutathione liquid dispersion that has undergone two low-temperature extraction processes and a liposomization process. Hereinafter, the manufacturing method of fermentation extracts using double low-temperature extraction and liposomization will be described in detail with reference to the attached drawings.

First, in a process of producing a liquid collagen extract at a low temperature, 5 parts by weight of collagen powder, 30 parts by weight of butylene glycol, and 65 parts by weight of purified water are mixed to produce a liquid collagen extract at a low temperature of 20° C. As an example, 300 g of butylene glycol+650 g of purified water+50 g of low-molecular weight collagen powder are mixed together (process step 1).

To explain in more detail the process of producing a liquid collagen extract at a low temperature, low-molecular weight collagen powder is prepared in a mesh screen of 400 mesh, and the temperature of an extractor is set to 20° C. A mesh screen containing 30 parts by weight of butylene glycol, 65 parts by weight of purified water, and 5 parts by weight of collagen powder is placed into the extractor, and extraction is performed for 250 to 300 hours. A completely extracted mixture is filtered (filtration process) through the mesh screen of 400 mesh to complete a liquid collagen extract extracted at a low temperature.

As shown in the Experimental Example illustrated in FIG. 1, as a result of the temperature-dependent extraction experiment performed with low-molecular weight collagen, the stability was the best when the temperature of the extractor was 20° C. based on the extraction time of 100 hours. However, even in this case, it can be seen that a precipitation phenomenon occurred from 40th day. Therefore, based on the Experimental Example in FIG. 1, an additional experiment was conducted as shown in FIG. 2 to derive an optimal extraction time at 20° C., and it was confirmed that the stability was the best when the extraction time was 250 hours and 300 hours. Finally, extraction of low-molecular weight collagen powder was performed for 250 to 300 hours by using a butylene glycol solvent and setting the temperature of the extractor to 20° C. to complete a liquid collagen extract extracted at a low temperature. The purified water described in the present invention may be prepared with reference to FIG. 8.

Next, in the process of producing a liposomized glutathione liquid dispersion, 90 parts by weight of purified water and 10 parts by weight of glutathione powder are mixed and stirred to complete a liposomized glutathione liquid dispersion (process step 2).

To explain in more detail the process of producing a liposomized glutathione liquid dispersion, 90 parts by weight of purified water and 10 parts by weight of glutathione powder are prepared. The purified water prepared is primarily mixed with the glutathione in a stirrer for 30 minutes. In a liposomization process, a homogeneous dispersion is prepared by passing the primarily stirred mixed liquid through a ultra-high pressure emulsification process (microfluidizer, M/F) and thereby finely pulverizing particles. The resulting homogeneous dispersion is filtered with a filter screen of 250 mesh to finally complete a liposomized glutathione liquid dispersion.

As shown in the Experimental Example illustrated in FIG. 3, when glutathione powder was dissolved in purified water, precipitation occurred from the first day as shown in the experimental data, causing difficulties in the process. Accordingly, a liposome glutathione raw material was prepared using a liposome method with high dissolution stability, and an experiment was performed using the liposome glutathione raw material. As a result, as shown in FIG. 4, the liposome glutathione was stable from a low content to a high content after the 20th day. Accordingly, it was decided to use a high-content liposomal glutathione 10% solution, which was stable from the first day. Finally, a liposomed glutathione liquid dispersion was completed through a liposomization process using purified water and glutathione powder.

Next, in the process of producing a *Lactobacillus* fermentation filtrate, 50 parts by weight of purified water, 30 parts by weight of a *Lactobacillus* fermentation solution, and 20 parts by weight of glycerin are mixed and fermented in a fermenter to complete a *Lactobacillus* fermentation filtrate (process step 3).

To explain in more detail the process of producing a *Lactobacillus* fermentation filtrate, a *Lactobacillus* strain is prepared, inoculated to a liquid medium, and incubated in an incubator for 3 days while maintaining the temperature of the liquid medium at to 40° C. so that the bacteria may grow well. 50 parts by weight of purified water, 30 parts by weight of a *Lactobacillus* fermentation solution, and 20 parts by weight of glycerin are added to the fermenter and fermented at 37° C. for ten hours. The completely fermented product is filtered through a mesh screen of 400 mesh to complete a *Lactobacillus* fermentation filtrate.

As shown in the Experimental Example shown in FIG. 5, off-flavor generation results according to each fermentation time were obtained from the strain fermentation solution obtained through the culturing process of the *Lactobacillus* strain using a liquid medium at 37° C. As shown in the Experimental Data, as the fermentation time increased, the stability decreased and off-flavors were generated, so the fermentation time after the culture was decided to be ten hours. Finally, fermentation was performed in a fermenter at 37° C. for ten hours to complete a *Lactobacillus* fermentation filtrate.

Next, in a process of producing a fermentation extract, the liquid collagen extract extracted in the process step 1 is used as a solvent to stirring and extracting the liposomized glutathione liquid dispersion of the process step 2 and the *Lactobacillus* fermentation filtrate of the process step 3 at a low temperature, thereby completing a fermentation extract (process step 4).

To explain in more detail the process of producing a fermentation extract, the temperature of an extractor is set to 25° C. The difference is that the low temperature is set to 20° C. in the process step 1, while the low temperature is set to 25° C. in the process step 4. 60 parts by weight of the liquid collagen extract prepared in the process step 1, which is a solvent, parts by weight of the liposomal glutathione liquid dispersion prepared in the process step 2, and 20 parts by weight of the *Lactobacillus* fermentation filtrate prepared in the process step 3 are added to the extractor and mixed. Because three raw materials with different characteristics are extracted along with a stirring process, extraction is performed in the extractor for 300 hours along with a stirring process (approximately 20 rpm). The completely extracted extract is filtered through a mesh screen of 400 mesh to finally complete a fermentation extract. In the process step 4, a process was used to extract the final products of the process step 2 and the process step 3 at a low temperature once again using liquid collagen, which is an extract from the process step 1, rather than purified water, as a solvent, and the low-temperature extraction conditions of the process step 4 are different from the low-temperature extraction conditions of the process step 1.

As shown in the Experimental example illustrated in FIG. 6, the three final materials obtained in the process steps 1, 2, and 3 were compositely mixed into a single mixture to complete the final process. Since the stability at 20° C. and 30° C. was relatively excellent, an intermediate value of these temperature values was set. A second experiment was performed to obtain the result values according to the elapse of extraction time, and excellent stability was confirmed as a result of extraction at 25° C. for 300 hours as shown in FIG. 7. Finally, extraction was performed at an extractor temperature of 25° C. and an extraction time of 300 hours to complete a final fermentation extract.

The finally produced fermentation extract may be inserted as an ingredient of a cosmetic composition to increase whitening and moisturizing effects.

In explaining the present invention, the description of conventional technologies and matters that are obvious to those skilled in the art may be omitted, and the description of these omitted components (methods) and functions may be sufficiently referred without departing from the technical idea of the present invention. In addition, the components of the present invention described above are only described for the convenience of explaining the present invention, and components not described herein may be added without departing from the technical idea of the present invention.

The description of the components and functions of each portion described above is explained separately from each other for convenience of explanation, and according to the need, one component and function may be implemented by integrating with other components, or may be implemented in further detail.

As described above, the present invention has whitening and moisturizing enhancement effects.

Although the present invention has been described above with reference to one embodiment, the present invention is not limited thereto, and various modifications and applications are possible. In other words, those skilled in the art will easily understand that many modifications are possible without departing from the gist of the present invention. In addition, it should be noted that when a specific description of the known functions and their components related to the present invention or the combination relationship between each component of the present invention is judged to unnecessarily obscure the gist of the present invention, the detailed description has been omitted.

The invention claimed is:

1. A fermentation extract consisting of a glutathione liquid dispersion liposomized using a liquid collagen extract as a solvent and a *Lactobacillus* fermentation filtrate obtained by stirring and extracting the same at a preset low temperature.

2. The fermentation extract according to claim 1, wherein the preset low temperature is 25° C.

3. The fermentation extract according to claim 1, wherein the liquid collagen extract is extracted at a low temperature of 20° C. by mixing collagen powder, butylene glycol, and purified water at a preset ratio.

4. The fermentation extract according to claim 1, wherein the liposomized glutathione liquid dispersion is a dispersion obtained by mixing and stirring purified water and glutathione powder at a preset ratio.

5. The fermentation extract according to claim 1, wherein the *Lactobacillus* fermentation filtrate is a filtrate obtained by mixing purified water, a *Lactobacillus* fermentation solution, and glycerin at a preset ratio and fermenting.

6. A cosmetic composition comprising a fermentation extract of claim 1.

7. A manufacturing method of a fermentation extract using dual low-temperature extraction and liposomization, the method comprising:

a step of producing a liquid collagen extract at a first low temperature by mixing collagen powder, butylene glycol, and purified water at a preset ratio;

a step of producing a liposomized glutathione liquid dispersion by mixing and stirring purified water and glutathione powder at a preset ratio;

a step of producing a *Lactobacillus* fermentation filtrate obtained by mixing purified water, a *Lactobacillus* fermentation solution, and glycerin at a preset ratio and fermenting; and a step of producing a fermentation extract by stirring and extracting a glutathione liquid dispersion liposomized using a liquid collagen extract as a solvent and a *Lactobacillus* fermentation filtrate at a second low temperature which is different from the first low temperature.

8. The manufacturing method of a fermentation extract according to claim 7, wherein the step of producing a liquid collagen extract includes:

a step of preparing low-molecular-weight collagen powder in a mesh screen of 400 mesh;

a step of setting the temperature of an extractor to 20° C.;

a step of placing a mesh screen containing 30 parts by weight of butylene glycol, 65 parts by weight of purified water, and 5 parts by weight of collagen powder into the extractor;

a step of extracting in the extractor for 250 to 300 hours; and a step of filtering a completely extracted mixture through the mesh screen of 400 mesh to complete a liquid collagen extract extracted at a low temperature.

9. The manufacturing method of a fermentation extract according to claim 7, wherein the step of producing a liposomized glutathione liquid dispersion includes:

a step of preparing 90 parts by weight of purified water and 10 parts by weight of glutathione powder;

a step of primarily mixing the purified water with the glutathione in a stirrer for 30 minutes;

a step of producing a homogeneous dispersion by passing the primarily stirred mixed liquid through a ultra-high pressure emulsification process; and a step of filtering the homogeneous dispersion with a filter screen of 250 mesh to complete a liposomized glutathione liquid dispersion.

10. The manufacturing method of a fermentation extract according to claim 7, wherein the step of producing a *Lactobacillus* fermentation filtrate includes:

a step of producing a *Lactobacillus* fermentation solution by preparing a *Lactobacillus* strain, inoculating the same into a liquid medium, maintaining the temperature of the liquid medium at 35 to 40° C., and culturing in an incubator for three days;

a step of adding 50 parts by weight of purified water, 30 parts by weight of the *Lactobacillus* fermentation solution, and 20 parts by weight of glycerin into a fermenter and fermenting at 37° C. for ten hours; and a step of filtering the completely fermented product through a mesh screen of 400 mesh to complete a *Lactobacillus* fermentation filtrate.

11. The manufacturing method of a fermentation extract according to claim 7, wherein the step of producing a fermentation extract includes:

a step of setting the temperature of an extractor to 25° C.;

a step of adding 60 parts by weight of a liquid collagen extract as a solvent, 20 parts by weight of liposomized glutathione liquid dispersion, and 20 parts by weight of the *Lactobacillus* fermentation filtrate into the extractor and mixing;

a step of extracting for 300 hours while performing a stirring process; and a step of filtering the completely extract through a mesh screen of 400 mesh to complete a fermentation extract.

* * * * *